United States Patent
Yang

(10) Patent No.: US 7,109,364 B2
(45) Date of Patent: Sep. 19, 2006

(54) GROUP OF ANTI-CANCER COMPOUNDS WITH SPECIFIC STRUCTURE AND THEIR PRODUCTION METHOD

(76) Inventor: Zhenhua Yang, 3008 Andalucia Dr., West Covina, CA (US) 91791

( * ) Notice: Subject to any disclaimer, the term of this patent is extended or adjusted under 35 U.S.C. 154(b) by 482 days.

(21) Appl. No.: 10/181,444

(22) PCT Filed: Feb. 7, 2001

(86) PCT No.: PCT/US01/00683

§ 371 (c)(1),
(2), (4) Date: Nov. 19, 2002

(87) PCT Pub. No.: WO01/59067

PCT Pub. Date: Aug. 16, 2001

(65) Prior Publication Data

US 2004/0034242 A1    Feb. 19, 2004

Related U.S. Application Data

(60) Provisional application No. 60/180,677, filed on Feb. 7, 2000, provisional application No. 60/222,148, filed on Aug. 1, 2000.

(51) Int. Cl.
*C07C 57/00* (2006.01)
(52) U.S. Cl. .................. 554/224; 514/558; 514/559; 514/675; 514/693; 514/724; 562/433; 562/553; 568/303; 568/579; 568/700

(58) Field of Classification Search ................ 554/224; 568/303, 579, 700; 514/558, 559, 675, 693, 514/724; 562/433, 553
See application file for complete search history.

(56) References Cited

U.S. PATENT DOCUMENTS 6,214,875 B1    4/2001    Yang

OTHER PUBLICATIONS

Abstr. of CN-1,282,730, 2000.*
Chem. Abstr. of Degtyarenko et al., "Fatty Aicds in extracts from Daphne bholus", 1988.*
Myers et al., "A Convergent Synthesis Route to the Tunicamycin Antiboiotics. Synthesis of (+)-Tunicmycin V", JACS, vol. 115, pp. 2036-2038, 1993.*
Stenfanov et al., "An Unusual Fatty Acid Composition For a Fresh-Water Mussel, UNIO TUMIDUS, Grom Bulgaria", Journal of Natural Products., vol. 55, No. 7, pp. 979-981, 1992.*
Ihn, et al., Chem. Abstract of 'On the structure of streptovirudin', Tetrahedron, vol. 38(12), pp. 1781-1785 (1982).

* cited by examiner

*Primary Examiner*—Deborah D. Carr
(74) *Attorney, Agent, or Firm*—Oblon, Spivak, McClelland, Maier & Neustadt, P.C.

(57) ABSTRACT

Compounds containing a specific branched chain end terminal group, which is isopropyl, sec.-butyl, or tert.-butyl; a polar leading group; and long-chain aliphatic, non-cyclic, saturated or unsaturated, hydrocarbon group linking them; and having anti-cancer and immune boosting activity.

5 Claims, No Drawings

GROUP OF ANTI-CANCER COMPOUNDS WITH SPECIFIC STRUCTURE AND THEIR PRODUCTION METHOD

BACKGROUND OF THE INVENTION

1. Field of the Invention

The invention is drawn to a group of compounds with specific structure, which possess anti-cancer activity. It also relates to processes of making these compounds, and processes for their use in human and other mammalian subjects for cancer therapy, prevention, and immune boosting functions.

2. Description of the Background

Extensive studies have been underway for over 2 decades to identify drugs that could be used to treat cancer. Drugs that either directly or indirectly cause tumor cell growth arrest, or cause tumor cell death via apoptotic mechanisms have been identified. However, major limiting factors in anticancer therapy still exist, i.e. drugs' adverse effects on normal cells and drug resistance developed by cancer cells. Some new approaches, such as anti-angiogenesis approach, represent new avenues of fighting cancer.

Nonetheless the most direct approach to stop cancer is to use drugs that kill tumor cells. As mentioned above, one major drawback of these conventional cancer-killing drugs is that they also kill non-cancerous cells and cause severe adverse effects. In an effort to search for anti-cancer agents that have minimal effects on normal tissue, a group of compounds with specific structure that directly kill cancer cells but do not harm normal cells have recently been identified.

A group of specific iso- and anteiso-branched-chain fatty acids with significant anti-cancer effect has been described in Applicant's U.S. application Ser. No. 09/173,681, now U.S. Pat. No. 6,214,875. Such compounds as described in the above Applicant's U.S. Application, and derivatives thereof obtained by reacting the acid moiety thereof, are described in Applicant's WO 99/53086. These compounds have shown excellent cytotoxic activity through induction of apoptosis against a broad variety of cancer cells, including, but not limited to, leukemia, breast cancer, prostate cancer, lung cancer, with extremely low toxicity to experimental animals.

JP-A 04295423 and JP-B 07072134, each to Daiichi, disclose anti-cancer agents containing $MeCHR(CH_2)_nCOOH$ wherein R is $C_1$–$C_5$ alkyl and n=4–22. U.S. Pat. No. 4,985,466 to Deguchi disclose a method for treating tumors susceptible to treatment with a wool fatty acid, or its reduced alcohol, metal salt or aliphatic ester derivative, or a wool alcohol, or its carboxylic acid, aliphatic ether or aliphatic ester derivative. Deguchi additionally disclose that it is characteristic of wool fatty acid and wool alcohol to contain a large quantity of iso- and anteiso- higher saturated aliphatic compounds. Deguchi also exemplifies a number of specific iso- and anteiso-higher saturated aliphatic acids and alcohols.

However, none of the above prior art recognizes Applicant's discovery that the anti-cancer activity resides in a terminal branch structure and a polar group per se directly linked at opposite ends, respectively, of a long chain group.

SUMMARY OF THE INVENTION

The present invention relates to a group of compounds with specific chemical structure, and possessing anti-cancer activity. This group of compounds are comprised of three parts: end-terminal group, leading group, and a long-chain aliphatic, non-cyclic, saturated or unsaturated, hydrocarbon group, defined in further detail below, to link them. The end-terminal group is isopropyl, sec.-butyl, or tert.-butyl group; it must be linked by a long-chain aliphatic, non-cyclic, saturated or unsaturated, hydrocarbon group, to the leading group; the leading group must be a polar group. The more polar it is, the stronger the anti-cancer activity will be. In addition, this group of compounds has cancer prevention and immune boosting functions without harmful side effects to humans and other mammalian subjects. The invention also relates to methods of producing these compounds. The above-mentioned specific group of compounds can be chemically synthesized. It is possible that they may exist in nature, non-isolated, e.g., in living organisms.

DETAILED DESCRIPTION OF THE INVENTION

The present invention is drawn to a specific group of compounds with unique chemical structure. This unique structure is comprised of three parts: end-terminal group, leading group, and a long-chain aliphatic, non-cyclic, saturated or unsaturated, hydrocarbon group to link them:

1. An end-terminal group of isopropyl:

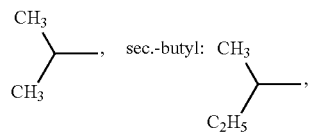

or tert.-butyl:

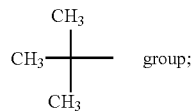

group;

2. The end-terminal group is linked to the leading group by a long-chain aliphatic, non-cyclic, saturated or unsaturated, hydrocarbon group, the length of which is at least 5 carbons, such as pentamethylene, and preferably between 5 and 19 carbons;

3. The leading group must be a polar group. The more polar this group is, the stronger the anti-cancer activity will be. When the leading group is non-polar, the compound will not have anti-cancer or cancer prevention or immune boosting functions.

This specific group of compounds can be represented by the following three formulae (1), (2) or (3):

(1)

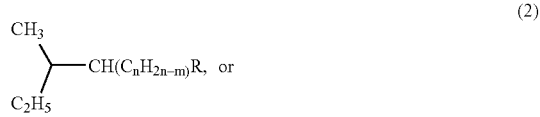
(2)

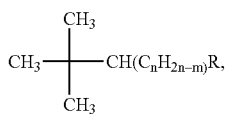

(3)

wherein n is an integer of at least 5, and preferably 5 to 19, m is an even integer from 0 to 2b, wherein b is the maximum number of unsaturated bonds (a double bond is counted as 1 and a triple bond is counted as 2), and R can be any polar group. However, to the extent R includes polar groups resulting in compounds disclosed by Daiichi or Deguchi, supra, or other unknown prior art, these compounds are excluded herein from the compounds claimed. Thus, excluded are compounds of formulae (1) and (2) wherein m=0, and R is COOH or an aliphatic ester thereof or salt thereof, or R is OH or an aliphatic ether thereof or aliphatic ester thereof.

In the present invention, R can be, but is not limited to, the following:

1: amide group, such as R=—$CONR_1R_2$ wherein $NR_1$ can be, but is not limited to, the following: hydroxyl-substituted phenylamine group (wherein the number of hydroxyl group(s) can be 1 to 5, and they can be linked to any possible position(s)); amino acid; aminoglucose; 3-hydroxyl4-carboxyl-phenylamine group; sulfonic phenylamine group; or amino heterocyclic group, while $R_2$ is hydrogen. Alternatively, $R_1$ and $R_2$ can independently be methyl or ethyl group; or $R_1$ and $R_2$ together with N can be a heterocyclic group, such as piperidine, pyrrolidine, morpholine, etc.

For example,

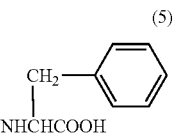

(1)

N-(3,4-Dihydroxyphenyl)-13-methyl tetradecanamide (2)

N-(4-Sulfo-phenyl)-13-methyl tetradecamide (3)

N-(13-Methyl-tetradecanoyl)glycine (4)

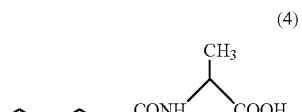

N-(13-Methyl-tetradecanoyl)-L-alanine

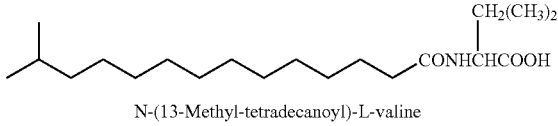

N-(13-Methyl-tetradecanoyl)-L-phenylalanine

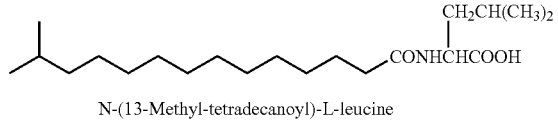

N-(13-Methyl-tetradecanoyl)-L-valine

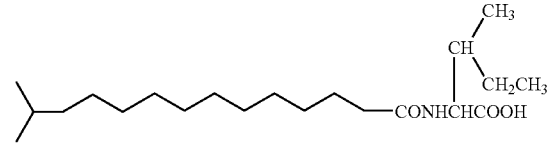

N-(13-Methyl-tetradecanoyl)-L-leucine

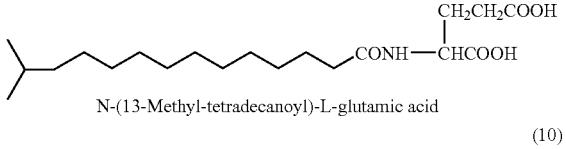

N-(13-Methyl-tetradecanoyl)-L-isoleucine

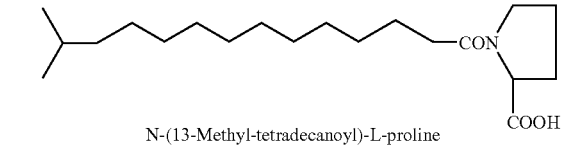

N-(13-Methyl-tetradecanoyl)-L-glutamic acid

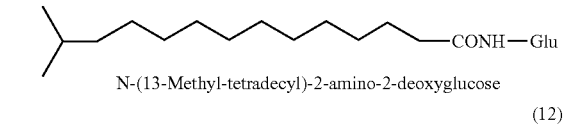

N-(13-Methyl-tetradecanoyl)-L-proline

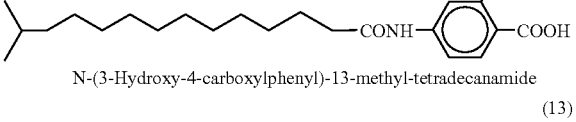

N-(13-Methyl-tetradecyl)-2-amino-2-deoxyglucose

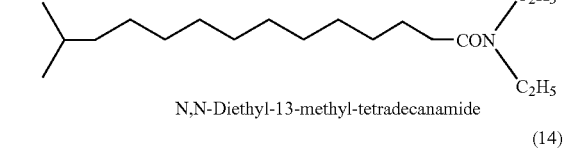

N-(3-Hydroxy-4-carboxylphenyl)-13-methyl-tetradecanamide

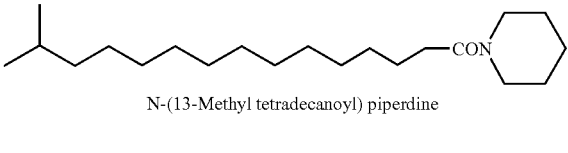

N,N-Diethyl-13-methyl-tetradecanamide (14)

N-(13-Methyl tetradecanoyl) piperdine

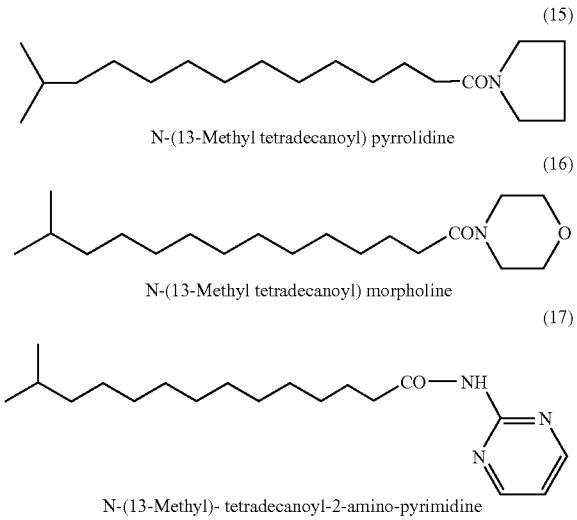

(15) N-(13-Methyl tetradecanoyl) pyrrolidine

(16) N-(13-Methyl tetradecanoyl) morpholine

(17) N-(13-Methyl)- tetradecanoyl-2-amino-pyrimidine

2: ester group, such as R=—COOR$_3$ wherein R$_3$ can be, but is not limited to, a phenyl group with substitution(s) of sulfonic, carboxyl, or 1–5 hydroxyl group(s), at any possible position(s).

For example,

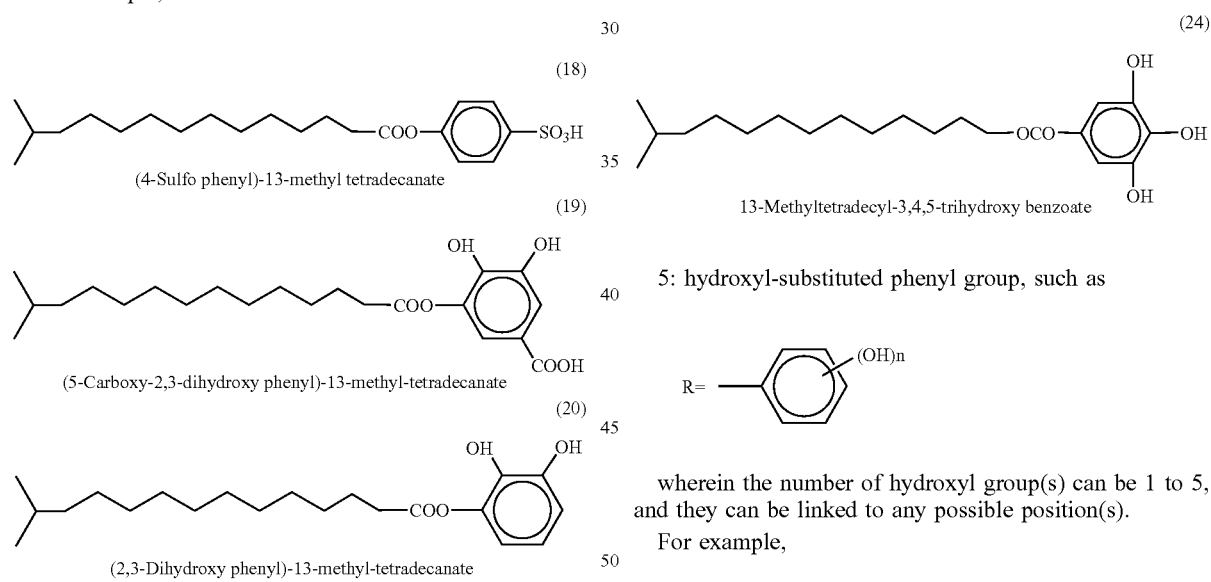

(18) (4-Sulfo phenyl)-13-methyl tetradecanate

(19) (5-Carboxy-2,3-dihydroxy phenyl)-13-methyl-tetradecanate

(20) (2,3-Dihydroxy phenyl)-13-methyl-tetradecanate

3: ketone group, such as R=—COR$_4$ wherein R$_4$ can be, but is not limited to, a phenyl group with substitution(s) of 1–5 hydroxyl group(s) at any possible position(s).

For example,

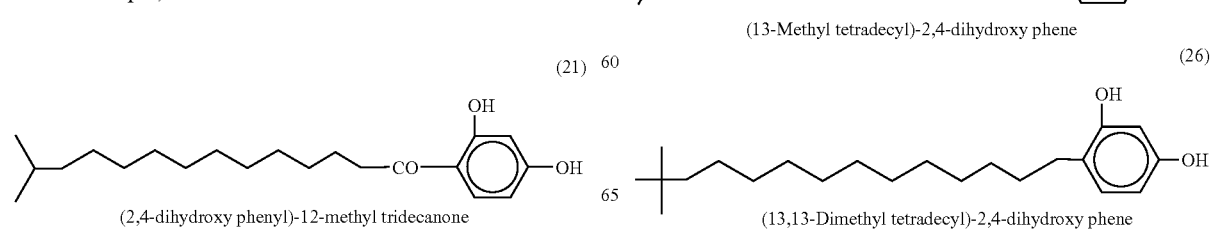

(21) (2,4-dihydroxy phenyl)-12-methyl tridecanone

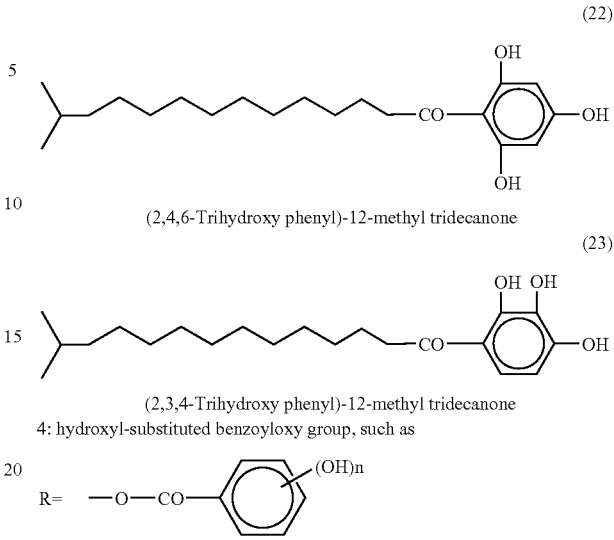

(22) (2,4,6-Trihydroxy phenyl)-12-methyl tridecanone

(23) (2,3,4-Trihydroxy phenyl)-12-methyl tridecanone

4: hydroxyl-substituted benzoyloxy group, such as

R= —O—CO—⬡—(OH)n wherein the number of hydroxyl group(s) can be 1 to 5, and they can be linked to any possible position(s).

For example,

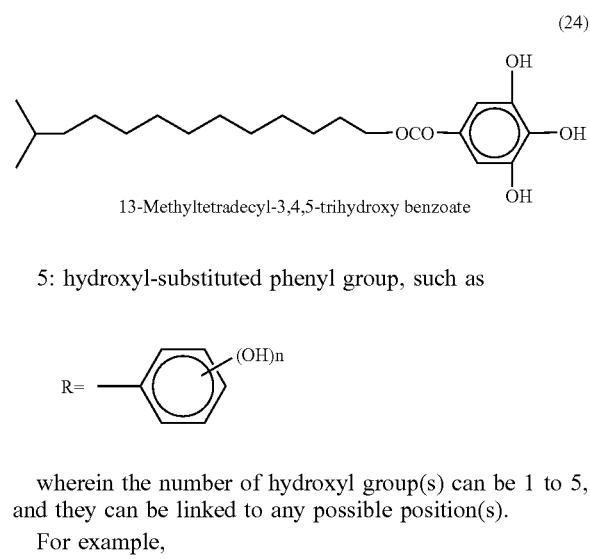

(24) 13-Methyltetradecyl-3,4,5-trihydroxy benzoate

5: hydroxyl-substituted phenyl group, such as

R= —⬡—(OH)n wherein the number of hydroxyl group(s) can be 1 to 5, and they can be linked to any possible position(s).

For example,

(25) (13-Methyl tetradecyl)-2,4-dihydroxy phene

(26) (13,13-Dimethyl tetradecyl)-2,4-dihydroxy phene

-continued (27)

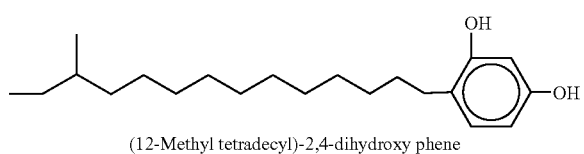

(12-Methyl tetradecyl)-2,4-dihydroxy phene (28)

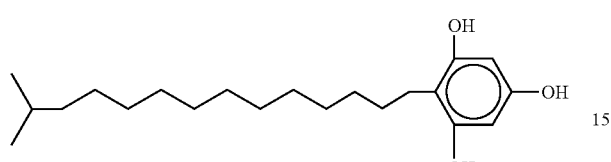

(13-Methyl tetradecyl)-2,4,6-trihydroxy phene (29)

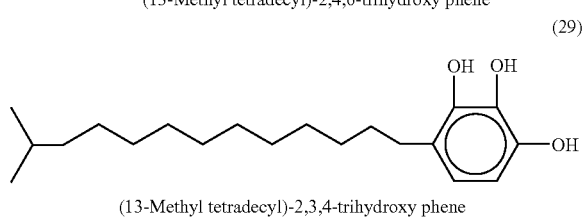

(13-Methyl tetradecyl)-2,3,4-trihydroxy phene

6: amine group, such as (1) R=—NH$_5$ or their physiologically acceptable salt, e.g., hydrochloric acid or sulfonic acid salt, etc.; wherein R$_5$ can be, but is not limited to, methyl, ethyl, hydroxyethyl, or a phenyl group, with substitution(s) of sulfonic, carboxyl, or 1–5 hydroxyl group(s), at any possible position(s).

For example, (30)

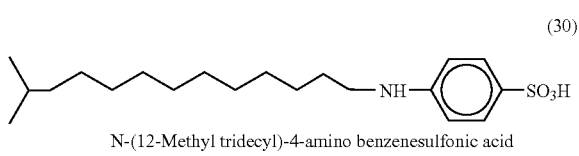

N-(12-Methyl tridecyl)-4-amino benzenesulfonic acid (31)

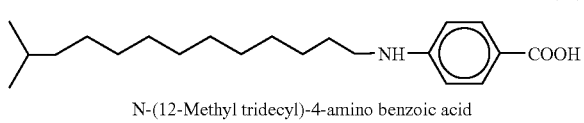

N-(12-Methyl tridecyl)-4-amino benzoic acid (32)

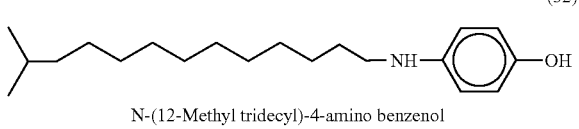

N-(12-Methyl tridecyl)-4-amino benzenol (33)

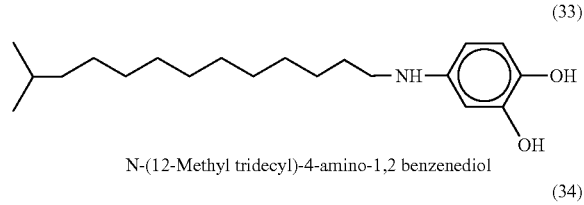

N-(12-Methyl tridecyl)-4-amino-1,2 benzenediol (34)

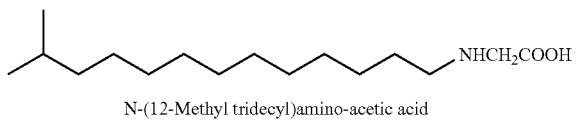

N-(12-Methyl tridecyl)amino-acetic acid

-continued (2)

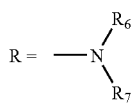

or their physiologically acceptable salt, e.g., hydrochloric acid or sulfonic acid salt, etc.; wherein R$_6$, R$_7$ can be, but are not limited to, methyl, ethyl, hydroxyethyl group, etc.

For example, (35)

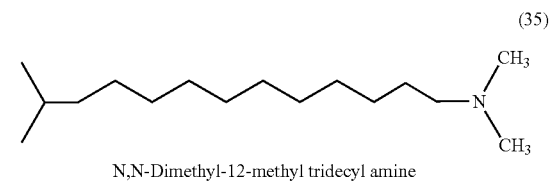

N,N-Dimethyl-12-methyl tridecyl amine (36)

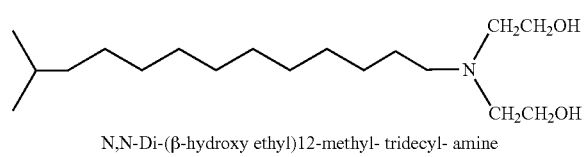

N,N-Di-(β-hydroxy ethyl)12-methyl- tridecyl- amine

7: amino-acyl group, such as

R=—NH—CO—R$_8$, wherein R$_8$ can be, but is not limited to, a phenyl group with substitution(s) of sulfonic, carboxyl, or 1–5 hydroxyl group(s), at any possible position(s).

For example, (37)

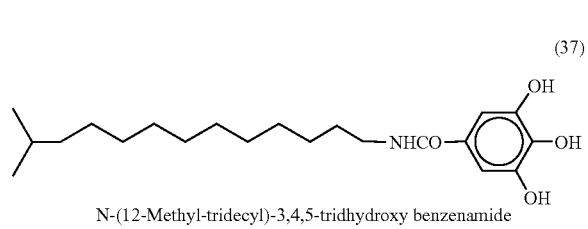

N-(12-Methyl-tridecyl)-3,4,5-tridhydroxy benzenamide

8: α-substituted carboxylic group, such as formula:

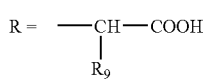

where R$_9$ can be, but is not limited to, halogen (fluorine, chlorine, bromine, iodine), amino, hydroxyl group, etc.

For example, (38)

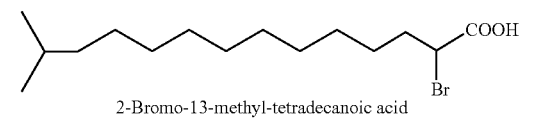

2-Bromo-13-methyl-tetradecanoic acid

-continued (39)

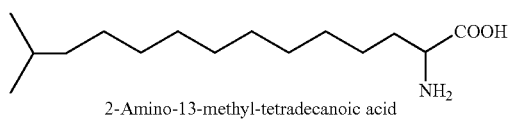

2-Amino-13-methyl-tetradecanoic acid

9: heterocyclic group, such as
For example, (40)

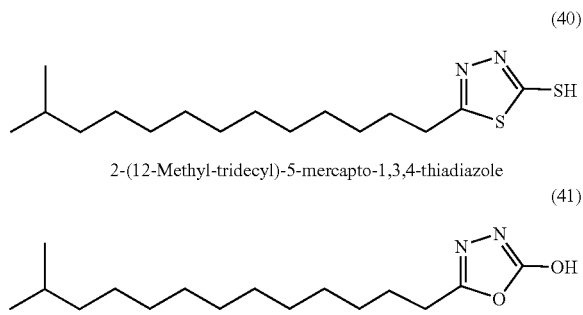

2-(12-Methyl-tridecyl)-5-mercapto-1,3,4-thiadiazole (41)

2-(12-Methyl-tridecyl)-5-hydroxy-1,3,4-oxadiazole

The compounds with specific structure also include unsaturated branched-chain fatty acids, and their pharmaceutically acceptable esters and metal salts. Particularly, those unsaturated branched-chain fatty acids with a double bond between the α and β carbons from the carboxyl end have stronger anticancer activity than other acids with a double bond at different positions.

For example, (42)

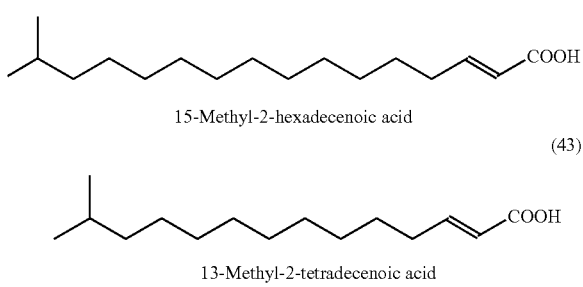

15-Methyl-2-hexadecenoic acid (43)

13-Methyl-2-tetradecenoic acid

The above-mentioned specifically-structured compounds can be chemically synthesized. Chemical synthesis can be carried out according to, but not limited to, the following methods:

1. In the specific structure of the current invention, the aliphatic long chain with end-terminal isopropyl or sec.-butyl group can be obtained from corresponding iso- or anteiso-fatty acids, respectively; the aliphatic long chain with end terminal tert.-butyl group can be obtained from corresponding fatty acids with end-terminal tert.-butyl group. Long chain fatty acids with an end-terminal tert.-butyl group can be synthesized from the monoester of the corresponding long chain diacid and a short chain fatty acid with end-terminal tert.-butyl group. Monoester of the long chain fatty acid with an end-terminal tert.-butyl group can be produced following electrolysis with the presence of sodium methoxide in anhydrous methanol, and can be hydrolyzed to yield the desired fatty acid in the presence of NaOH.

The following equation shows the synthesis of 13,13-dimethyl-tetradecanoic acid as an example:

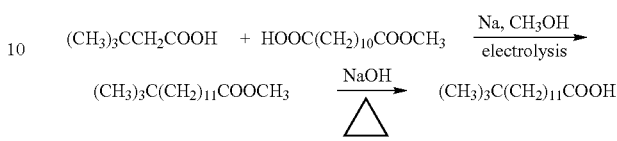

Example 1 has the details of the procedure.

2. In the specific structure of the current invention, when the leading group R is amide derivative, $-CONR_1R_2$:

Corresponding fatty acid reacts with dichlorosulfoxide to yield acyl chloride, and the latter can react with amino acid, amino-glucose, diethylamine, piperidine, pyrrolidine, morpholine, amino-phenol, amino-benzoic acid, or amino-benzenesulfonic acid to yield the desired product.

The following equation shows the synthesis of N-(13-methyl-tetradecanoyl)4-amino-1,2-benzenediol[N-(3,4Di-hydroxyphenyl)-13-methyl tetradecanamide] as an example:

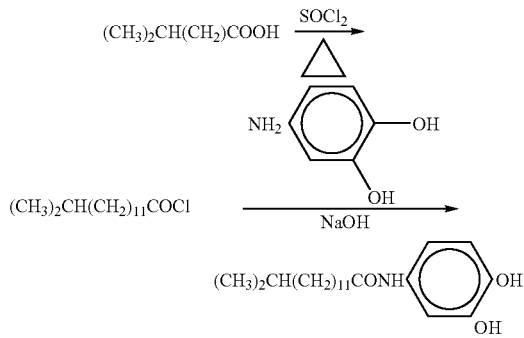

Example 2 has the details of the procedure.

3. In the specific structure of the current invention, when the leading group R is ester derivative, $-COOR_3$:

Corresponding fatty acid reacts with dichlorosulfoxide to yield acyl chloride, and the latter can react with hydroxy-benzoic acid, or hydroxy-benzenesulfonic acid to yield the desired product.

The following equation shows the synthesis of (4-sulfo phenyl)-13-methyl tetradecanate as an example:

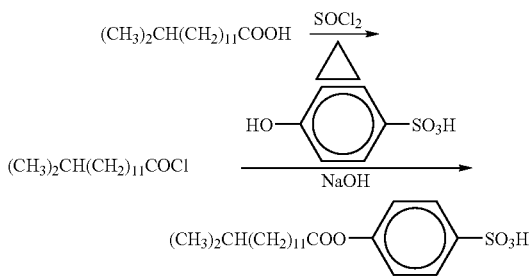

4. In the specific structure of the current invention, when the leading group R is ketone derivative, $-COR_4$:

Corresponding fatty acid reacts with 1,3-benzenediol to yield desired product with the catalysis of a Lewis acid.

The following equation shows the synthesis of (2,4-dihydroxy phenyl)-12-methyl tridecanone as an example:

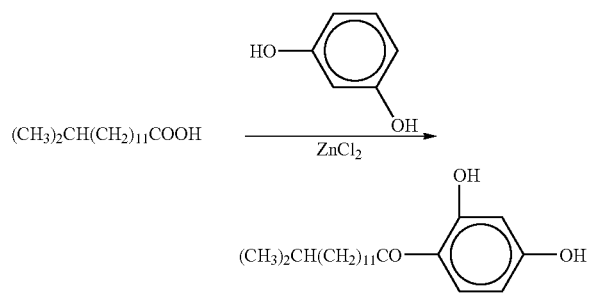

5. In the specific structure of the current invention, when the leading group R is hydroxyl-substituted phenyl derivative:

Corresponding hydroxylphenyl aliphatic ketone can be synthesized following method in 4 above, and can be reduced in the presence of zinc dust and hydrochloric acid to yield the desired product.

The following equation shows the synthesis of (13-methyl-tetradecyl)-2,4-dihydroxy phene as an example:

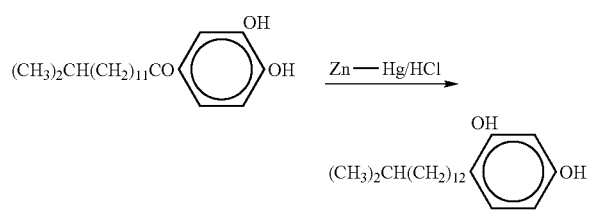

Example 7 has the details of the procedure.

6. In the specific structure of the current invention, when the leading group R is hydroxyl-substituted benzoyloxy derivative:

The methyl monoester of the corresponding fatty acid can be reduced to the respective alcohol with sodium and anhydrous methanol, the latter then reacts in an esterification reaction with hydroxyl-substituted benzoic acid in the presence of HCl under reflux with toluene and water to yield the desired product.

The following equation shows the synthesis of 13-methyltetradecyl-3,4,5-trihydroxy benzoate as an example:

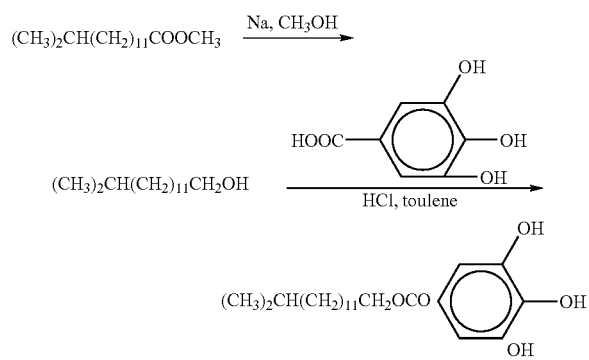

Example 8 has the details of the procedure.

7. In the specific structure of the current invention, when the leading group R is amine derivative, two kinds of methods can be applied:

(1) The methyl monoester of the corresponding fatty acid can be reduced to the respective alcohol with sodium and anhydrous methanol; the latter can then react with dichlorosulfoxide to yield alkyl chloride. Alkyl chloride can react with the amine derivative to yield the desired product.

The following equation shows the synthesis of N-(13-methyl-tetradecyl)4-amino-1,2-benzenediol as an example:

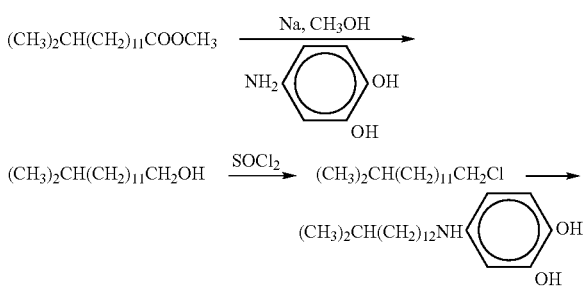

(2) Corresponding fatty acid can be converted to amide, and amide rearranges to give amine in the presence of bromine and sodium methoxide. Amine then reacts with chloro-derivatives to yield the desired product.

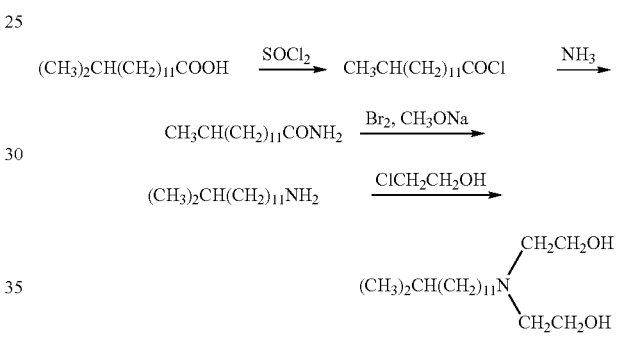

Example 6 has the details of the procedure.

8. In the specific structure of the current invention, when the leading group R is amino-acyl derivative:

These compounds can be synthesized by reaction between amine (described above in 7) and the methyl monoester of the corresponding carboxylic acid.

The following equation shows the synthesis of N-(12-methyl-tridecyl)-3,4,5-trihydroxy benzenamide as an example:

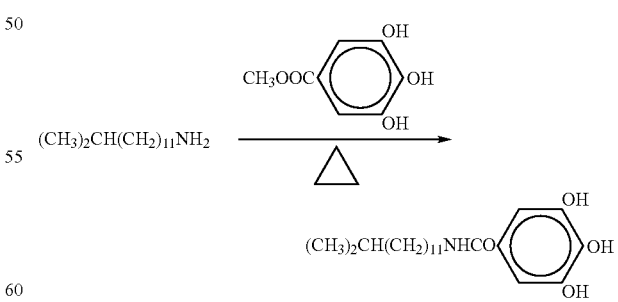

9. In the specific structure of the current invention, when the leading group R is α-substituted carboxylic derivative:

Corresponding fatty acid can react with bromine to yield α-bromo fatty acid, which then reacts with ammonia water to yield α-amino derivatives.

The following equation shows the synthesis of 2-amino-13-methyl-tetradecanoic acid as an example:

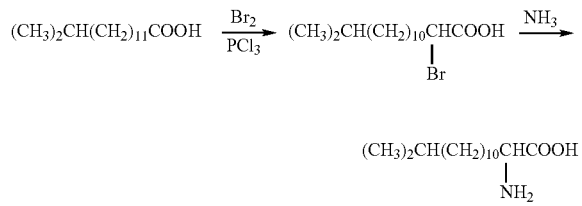

10. In the specific structure of the current invention, when the compounds are unsaturated branched-chain fatty acids with a double bond between α and β carbons from the carboxyl end:

The methyl monoester of the corresponding fatty acid can be reduced to the respective alcohol with sodium and anhydrous methanol, the latter can then be oxidized to aldehyde in the presence of a pyridine salt of chloro-chromic acid. The aldehyde can then be decarboxylated in a condensation reaction in the presence of malonic acid to yield the desired product.

The following equation shows the synthesis of 15-methyl-2-hexadecenoic acid as an example:

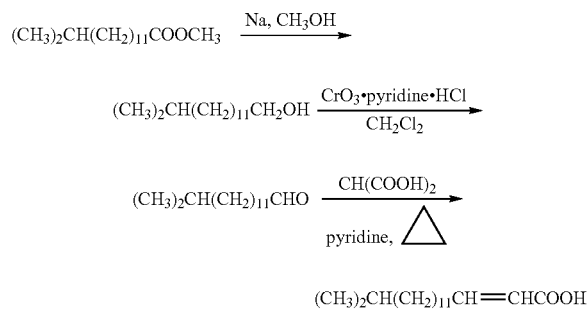

Example 5 has the details of the procedure.

Having generally described this invention, a further understanding can be obtained by reference to certain specific examples which are provided herein for purposes of illustration only and are not intended to be limiting unless otherwise specified. Examples demonstrating efficacy of the compounds of the present invention are referred to as "Experiments;" examples demonstrating preparation of the compounds of the present invention are referred to as "Examples."

EXPERIMENTS

Experiment 1

In Vitro Anti-Cancer Efficacy Comparison

Reagents: In vitro anti-cancer activities of the following compounds were compared, which are characterized by the presently-disclosed structure and synthesized by the presently-disclosed process. They include N-(3,4-Dihydroxyphenyl)-13-methyl tetradecanamide, N-(4-Sulfo-phenyl)-13-methyl tetradecamide, N-(13-methyl-tetradecanoyl) glycine, N-(13-methyl-tetradecanoyl)-L-alanine, N-(13-methyl-tetradecanoyl)-L-phenylalanine, N-(13-methyl tetradecanoyl)-L-valine, N-(13-methyl-tetradecanoyl)-L-leucine, N-(13-methyl-tetradecanoyl)-L-isoleucine, N-(13-methyl-tetradecanoyl)-L-glutamic acid, N-(13-methyl-tetradecanoyl)-L-proline, N-(13-methyl-tetradecanoyl)-2-amino-2-deoxyglucose, N(3-Hydroxy-4-carboxyphenyl)-13-methyl-tetradecanamide, N,N-Diethyl-13-methyl-tetradecanamide, N-(13-Methyl tetradecanoyl)piperidine, N-(13-Methyl-tetradecanoyl)pyrrolidine, N-(13-Methyl-tetradecanoyl)morpholine, N-(13-Methyl-tetradecanoyl)-2-amino-pyrimidine, (2,4,-dihydroxy phenyl)-12-methyl tridecanone, (2,4,6-Trihydroxy phenyl)-12-methyl tridecanone, (2,3,4-Trihydroxy phenyl)-12-methyl tridecanone, (13-Methyl tetradecyl)-2,4-dihydroxy phene, (13,13-Dimethyl tetradecyl)-2,4-dihydroxy phene, (12-Methyl tetradecyl)-2,4-dihydroxy phene, (13-Methyl tetradecyl)-2,3,4-trihydroxy phene, N-(12-Methyl tridecyl)-4-amino benzenesulfonic acid, N-(12-Methyl-tridecyl) amino-1,2-benzenediol, 2-Bromo-13-methyl-tetradecanoic acid, 2-Amino-13-methyl-tetradecanoic acid, 15-Methyl-2-hexadecenoic acid, 2-(12-Methyl-tridecyl)-5-mercapto-1,3,4-thiadiazole, 13,13-Dimethyl-tetradecanoic acid, N-(13-Methyl tetradecyl)4amino-1,2-benzenediol, and 9-Methyl-2-decenoic acid.

The above compounds were dissolved in DMSO at stock concentration of 10 mg/ml and stored at 4° C. Before each experiment they were diluted to desired concentration with serum-free RPMI 1640 medium Methods:

1. K562 human leukemia cell line: K562 cells were maintained in RPMI 1640 medium with 5% fetal bovine serum at 37° C. under 5% $CO_2$ atmosphere. $4 \times 10^4$ cells/well were plated on 96-well plate. After treatment with the test compounds and solvent control (DMSO) for 48 hours, numbers of live cells were counted by trypan blue dye exclusion. $IC_{50}$ and $IC_{90}$ were calculated by Bliss method and listed in Table 1.

2. B16 mouse melanoma cell line: B16 cells were maintained under the same condition as above. $2 \times 10^4$ cells/well were plated on 48-well plate and left for 12 hours for attachment. Cells were then treated with the test compounds and solvent control for 48 hours. Numbers of live cells were determined by SRB method. Briefly, cells were fixed with 50 μl/well 15% TCA for 1 hour, and then washed three times with double-distilled water. After drying 50 μl/well 1% SRB dye was added and reacted for 10 minutes. Plate was washed with 1% acetic acid. 0.2 ml Tris buffer (pH 9.6) was added and $OD_{510}$ was recorded. $IC_{50}$ and $IC_{90}$ were calculated and listed in Table 1.

TABLE 1

$IC_{50}$ and $IC_{90}$ (μg/ml) for K562 and B16

| | Compounds | K562 | | B16 | |
| --- | --- | --- | --- | --- | --- |
| | | $IC_{90}$ | $IC_{50}$ | $IC_{90}$ | $IC_{50}$ |
| 1 | N-(3,4-Dihydroxyphenyl)-13-methyl tetradecanamide | 10.1 | 4.98 | 9.28 | 5.12 |
| 2 | N-(4-Sulfo-phenyl)-13-methyl tetradecamide | 37.8 | 27.1 | 35.7 | 25.4 |
| 3 | N-(13-methyl-tetradecanoyl) glycine | 21.9 | 14.7 | 20.1 | 12.8 |
| 4 | N-(13-methyl-tetradecanoyl)-L-alanine | 20.7 | 11.2 | 18.4 | 14.8 |
| 5 | N-(13-methyl-tetradecanoyl)-L-phenylalanine | 19.6 | 10.3 | 20.5 | 13.4 |
| 6 | N-(13-methyl-tetradecanoyl)-L-valine | 22.5 | 18.1 | 19.2 | 11.7 |

TABLE 1-continued

IC$_{50}$ and IC$_{90}$ (μg/ml) for K562 and B16

| | | K562 | | B16 | |
|---|---|---|---|---|---|
| | Compounds | IC$_{90}$ | IC$_{50}$ | IC$_{90}$ | IC$_{50}$ |
| 7 | N-(13-methyl-tetradecanoyl)-L-leucine | 30.6 | 11.8 | 20.1 | 10.4 |
| 8 | N-(13-methyl-tetradecanoyl)-L-isoleucine | 28.6 | 19.3 | 18.9 | 11.1 |
| 9 | N-(13-methyl-tetradecanoyl)-L-glutamic acid | 37.9 | 28.2 | 35.1 | 26.3 |
| 10 | N-(13-methyl-tetradecanoyl)-L-proline | 25.3 | 17.2 | 17.3 | 15.2 |
| 11 | N-(13-methyl-tetradecanoyl)-2-amino-2-deoxyglucose | 38.1 | 24.3 | 34.6 | 24.5 |
| 12 | N-(3-Hydroxy-4-carboxylphenyl)-13-methyl-tetradecanamide | 24.7 | 18.7 | 22.9 | 16.5 |
| 13 | N,N-Diethyl-13-methyl-tetradecanamide | 42.4 | 9.10 | 31.9 | 19.3 |
| 14 | N-(13-Methyl tetradecanoyl) piperidine | 38.5 | 18.4 | 33.7 | 17.2 |
| 15 | N-(13-Methyl-tetradecanoyl) pyrrolidine | 25.0 | 16.2 | 17.3 | 13.1 |
| 16 | N-(13-Methyl-tetradecanoyl) morpholine | 20.4 | 15.9 | 19.2 | 11.9 |
| 17 | N-(13-Methyl-tetradecanoyl)-2-amino-pyrimidine | 19.2 | 14.8 | 18.6 | 12.3 |
| 18 | (2,4,-dihydroxy phenyl)-12-methyl tridecanone | 8.90 | 6.42 | 8.12 | 5.91 |
| 19 | (2,4,6-Trihydroxyphenyl)-12-methyl tridecanone | 6.80 | 5.13 | 6.11 | 4.93 |
| 20 | (2,3,4-Trihydroxy phenyl)-12-methyl tridecanone | 20.2 | 15.3 | 19.32 | 14.8 |
| 21 | (13-Methyl tetradecyl)-2,4-dihydroxy phene | 5.25 | 3.62 | 5.14 | 3.22 |
| 22 | (13,13-Dimethyl tetradecyl)-2,4-dihydroxy phene | 5.36 | 3.92 | 5.42 | 3.63 |
| 23 | (12-Methyl tetradecyl)-2,4-dihydroxy phene | 14.6 | 9.51 | 13.8 | 8.81 |
| 24 | (13-Methyl tetradecyl)-2,3,4-trihydroxy phene | 19.2 | 13.6 | 19.5 | 12.8 |
| 25 | N-(12-Methyl tridecyl)-4-amino benzenesulfonic acid | 20.0 | 15.1 | 18.8 | 13.5 |
| 26 | N-(12-Methyl-tridecyl)-4-amino-1,2-benzenediol | 13.5 | 6.73 | 12.6 | 5.81 |
| 27 | 2-Bromo-13-methyl-tetradecanoic acid | 10.1 | 7.21 | 11.2 | 6.10 |
| 28 | 2-Amino-13-methyl-tetradecanoic acid | 28.6 | 19.7 | 25.3 | 17.4 |
| 29 | 15-Methyl-2-hexadecanoic acid | 10.1 | 17.7 | 6.8 | 10.5 |
| 30 | 2-(12-Methyl-tridecyl)-5-mercapto-1,3,4-thiadiazole | 8.75 | 6.10 | 8.05 | 5.16 |
| 31 | 13,13-Dimethyl-tetradecanoic acid | 37.5 | 24.6 | 35.6 | 20.4 |
| 32 | N-(13-Methyl tetradecanoyl)-4-amino-1,2-benzenediol | 11.5 | 6.31 | 10.6 | 5.75 |
| 33 | 9-Methyl-2-decenoic acid | 26.7 | 51.2 | 40.5 | 91.0 |

In contrast, the specific structured compounds disclosed in the present invention are not toxic against normal human peripheral blood lymphocytes at a concentration above 400 μg/ml, while they have significant cytotoxicity on various human cancer cell lines at well below this concentration.

Furthermore the in vitro anti-cancer activity of 2-(12-Methyl-tridecyl)-5mercapto-1,3,4-thiadiazole has been tested on other human cancer cell lines, including human prostate cancer DU145, human gastric cancer SNU-1, human lung cancer H1688, human colon cancer HCT-116, human hepatocarcinoma SNU-423, human pancreatic cancer CRL-1687, human CNS cancer SF-268, human renal cancer Caki-1, and human melanoma SK-MEL-5. Using viability assessment by trypan blue dye exclusion and calculation of inhibition rate with linear regression, IC$_{90}$ of 2-(12-Methyl-tridecyl)-5-mercapto-1,3,4-thiadiazole on various cancer cell lines above were determined to range from 8.3 μg/ml to 23.2 μg/ml.

Experiment 2

In Vitro Anti-Cancer Efficacy Comparison (2)

The in vitro efficacy test was carried out to compare unsaturated branched chain fatty acid, 9-methyl-2-decenoic acid and 9-methyl-6-decenoic acid, as well as 15-methyl-2-hexadecenoic acid and 15-methyl-6-hexadecenoic acid. The results are shown in Table 2.

Reagents and Methods: same as in Experiment 1.

TABLE 2

In vitro anticancer activity comparison of unsaturated fatty acids

| | K562 | | B16 | |
|---|---|---|---|---|
| Compound | IC$_{50}$ | IC$_{90}$ | IC$_{50}$ | IC$_{90}$ |
| 9-methyl-decanoic acid | 55.5 | 87.0 | 97.0 | 280 |
| 9-methyl-6-decenoic acid | 50.8 | 83.0 | 90.0 | 269 |
| 9-methyl-2-decenoic acid | 26.7 | 51.2 | 40.5 | 91.0 |
| 15-methyl-hexadecanoic acid | 25.9 | 35.6 | 20.7 | 38.2 |
| 15-methyl-6-hexadecenoic acid | 23.8 | 30.5 | 21.3 | 35.2 |
| 15-methyl-2-hexadecenoic acid | 10.1 | 17.7 | 6.8 | 10.5 |

The above result suggests that the anticancer activity of unsaturated branched-chain fatty acid is stronger than that of its corresponding saturated one, and also for unsaturated branched-chain fatty acids, the closer the double bond is to the carboxyl end, the higher polarity the molecular has, and the greater the anti-cancer activity it has.

Experiment 3

In vivo Anti-Cancer Efficacy Comparison (Solid Tumor Model)

Mouse cervical carcinoma $U_{14}$ model was used to compare in vivo anti-cancer efficacy of 15-methyl-2-hexadecenoic acid, 13-methyl-tetradecanoic acid and the chemotherapy drug cytoxan (CTX).

Reagents and Methods:

40 male ICR strain mice, weighing 19–22 g, were randomly divided into 4 groups of 10 each. $U_{14}$ cervical carcinoma mass (about 2 mm$^3$ each) was transplanted subcutaneously into the right armpits of all animals following standard procedure. The test group was given 15-methyl-2-hexadecenoic acid and 13-methyl-tetradecanoic acid at 0.4 g/kg, respectively, intragastrically (i.g.) daily for 11 days. The positive control group was given a single dose of CTX i.g. (25 mg/kg) on day 1. Negative control group was given normal saline (N.S.) at 0.2 ml/10 g daily for 11 days. On the 12th day, all mice were sacrificed and the tumors were isolated and weighed. The tumor inhibition rate (TIR) was calculated and subject to t test. A comparison of the in vivo efficacy is shown in Table 3.

TABLE 3

In vivo Efficacy Comparison

| Group | Dosage | No. | Body W. (g, X ± SD) D$_1$ | Body W. (g, X ± SD) D$_{12}$ | Tumor W. (g, ± SD) | TIR % | p |
|---|---|---|---|---|---|---|---|
| N.S. | 20 ml/kg | 10 | 20.6 ± 0.7 | 24.8 ± 0.8 | 2.63 ± 0.29 | — | — |
| 13-methyl-tetradecanoic acid | 0.4 g/kg | 10 | 20.7 ± 0.7 | 26.0 ± 2.6 | 0.93 ± 0.32 | 64.6 | <0.05 |
| 15-methyl-2-hexadecenoic | 0.4 g/kg | 10 | 20.6 ± 0.7 | 25.5 ± 0.8 | 0.50 ± 0.29 | 81.0 | <0.05 |
| CTX | 25 mg/kg | 10 | 20.6 ± 0.5 | 22.6 ± 1.2 | 0.46 ± 0.17 | 82.5 | <0.05 |

The above results indicate that 15-methyl-2-hexadecenoic acid has comparable anticancer effect with CTX, and greater anticancer activity than that of saturated fatty acid. Judged by changes in body weights, no toxic effect was observed in animals treated with the test compounds of the present invention.

Experiment 4

In vivo Anti-Cancer Efficacy Comparison (Ascites Model)

Reagents and Methods:

30 female ICR strain mice, weighing 18–21 g, were randomly divided into 3 groups of 10 each. 0.2 ml of HAC cell suspension ($10^7$ cells/ml) was injected intraperitoneally (i.p.) into all animals. The test group was given 2-(12-Methyl-tridecyl)-5-mercapto-1,3,4-thiadiazole at 0.4 g/kg i.g. daily till death. The positive control group was given 5-Flurouracil (5-Fu) i.g. at 25 mg/kg on day 1, 3, and 5. The negative control group was given N.S. at 20 ml/kg daily as in test groups. The length of survival of each group was recorded and rate of extension of life span was calculated and subject to t test.

Results:

TABLE 4

Extension of life span of HAC mice by the sample

| Group | No. of mice | Body Weight (g, X ± SD) before treatment | Body Weight (g, X ± SD) after treatment | Survival Time (days, X ± SD) | Extension Rate (%) |
|---|---|---|---|---|---|
| N.S. 20 ml/kg (Control) | 10 | 19.5 ± 1.2 | 34.6 ± 3.8 | 9.7 ± 1.9 | — |
| 2-(12-Methyl-tridecyl)-5-mercapto-1,3,4-thiadiazole, 0.4 g/kg | 10 | 19.6 ± 1.3 | 46.5 ± 6.1 | 16.7 ± 1.8 | 72.2 |
| 5-FU 25 mg/kg (Positive Control) | 10 | 19.5 ± 1.2 | 43.4 ± 12.8 | 14.3 ± 1.5 | 47.4 |

Experiment 5

Therapeutic Effect of 13-methyl-2-tetradecenoic acid on Human Breast Carcinoma MCF7ras Xenografted into Nude Mice Reagents and Methods:

Thirty female Balb/c-nu/nu athymic mice, 6 weeks old, weighing 18–22 g, were housed in specific pathogen free (SPF) condition throughout the course of the experiment. Subcutaneous transplantation of human breast carcinoma MCF7ras was carried out under aseptic condition. Tumor mass was cut into fragments (approximately 0.18×0.18×0.20 mm in size), and injected s.c. into the right mammary fat pad of each animal with a trocar. The mice were randomized into control and test groups of ten mice each. The day after transplantation, the mice in the test group were given through gavage 13-methyl-2-tetradecenoic acid at 400 mg/kg daily. The mice in two control groups were administered with CTX at 25 mg/kg and N.S. at 0.2 ml/10 g. All animals were sacrificed on day 23. The body weights and tumor weights were measured. The tumor inhibition rates (TIR) were determined by comparing the mean tumor weight of the test groups (T) with that of the control group (C) and expressed as a (C-T)/C percentage, and were analyzed by Student's test for statistical significance. The results are shown in Table 5.

TABLE 5

Comparison of inhibition effects on transplanted human breast cancer MCF7ras

| Group | No. | Body weight (g, X ± SD) D$_1$ | Body weight (g, X ± SD) D$_{23}$ | Tumor W. (g, X ± SD) | TIR | p |
|---|---|---|---|---|---|---|
| N.S. 0.2 ml/10 g | 10 | 20.2 ± 0.6 | 21.5 ± 1.3 | 1.83 ± 0.53 | — | — |
| CTX 25 mg/kg | 10 | 20.4 ± 0.4 | 18.6 ± 0.2 | 0.43 ± 0.15 | 76.5 | <0.05 |
| 13-methyl-2-tetradecenoic acid | 10 | 20.3 ± 0.5 | 24.4 ± 1.1 | 0.47 ± 0.31 | 74.3 | <0.05 |

The results above showed significant inhibition effect of 13-methyl-2-tetradecenoic acid on human breast cancer MCF7ras while no toxic effect was observed from the body weight curve.

Experiment 6

13, 13-Dimethyl-tetradecanoic acid's Function in Preventing Ultraviolet B Ray (UVB)-Induced Skin Cancer 13, 13-Dimethyl-tetradecanoic acid (Sample) was encapsulated with liposome at a final concentration of 10%.

Thirty female SKH-1 hairless mice were randomly divided into control and test groups of 15 each. Each mouse in both groups was treated topically once with DMBA (5.12 μg dissolved in 200 μl acetone solution) to achieve tumor initiation. One week later (day 8), animals in test group started to receive topical application of 200 μl Sample solution once a day. Control group received 200 μl liposome solvent instead every day. Thirty minutes after the application, animals in both groups were exposed to UVB (290–320 mn) radiation at the dosage of 180 mJ/cm² per day to induce growth of tumor. The animals were evaluated for tumor development at the end of 30 weeks.

The results suggest that the Sample has a preventive effect when used during early stage of tumor induction. At the end of experiment, the animals in Sample-treated group showed a 65% reduction in tumor incidence compared to those in the control group. The average size of cancer in the Sample-treated group was also 87% smaller.

The compounds with the specific structure disclosed in present invention, including, but not limited to, 13, 13-Dimethyl-tetradecanoic acid, have cancer prevention function, not limited to skin cancer. Since these compounds have extremely low toxicity, they should be able to protect human and animal from cancer if taken regularly.

Experiment 7

Influence of N-(13-methyl-tetradecanoyl)4-amino-1,2-benzenediol on Immune Functions 1: Phagocytic Function of Reticuloendothelial System 50 female ICR strain mice, weighing 19–24 g, were randomly divided into 5 groups of 10 each. One group was given N.S. at 20 ml/kg i.g. as a normal control. A positive control group was given CTX i.g. at 25 mg/kg on day 1 and 6. A third group was given N-(13-methyl-tetradecanoyl)-4amino-1,2-benzenediol (Sample) only at 400 mg/kg i. g. The remaining two groups were given both CTX (25 mg/kg on day 1 and 6) and Sample (100 mg/kg and 400 mg/kg, respectively). All treatments except CTX were administered daily for 9 days. 30 minutes after the last administration, 0.15 ml Yidege (1:10) was injected into the tail vein of each mouse. 1 minute and 5 minutes after, blood was drawn and 20 μl serum was mixed with 0.1% $N_2CO_3$. $OD_{680}$ was measured and the clearance index $K=(1\ gOD_1-1\ gOD_2)/(t_2-t_1)$ was calculated. The results were subject to t test and shown in Table 6.

TABLE 6

Effects of Sample on Serum Clearance Index of Carbon Grain in Normal and Immune-compromised Mouse

| | | | P | |
|---|---|---|---|---|
| Group (i.g.) | No. of Mice | K (X ± SD) | Compared with Group 1 | Compared with Group 2 |
| N.S. 0.2 ml/10 g | 10 | 0.0782 ± 0.0342 | | <0.001 |
| CTX 25 mg/kg | 10 | 0.0238 ± 0.0161 | <0.001 | |
| Sample 400 mg/kg | 10 | 0.0812 ± 0.0290 | >0.05 | <0.001 |
| Sample 100 mg/kg + CTX 25 mg/kg | 10 | 0.0412 ± 0.0310 | <0.001 | <0.001 |
| Sample 400 mg/kg + CTX 25 mg/kg | 10 | 0.0543 ± 0.0410 | <0.001 | <0.001 |

The results in Table 6 demonstrate that N-(13-methyl-tetradecanoyl)-4-amino-1,2-benzenediol had no obvious effect on the Clearance Index of Carbon grain in normal mouse ($P_{1,3}$>0.05). Moreover the Sample could even improve the clearance of Carbon grain in CTX-treated mouse to a certain extent (both $P_{2,4}$ and $P_{2,5}$<0.01).

2: Serum Hemolysinogenesis 50 male ICR strain mice, weighing 20–23 g, were randomly divided into 5 groups of 10 each. The method of administration in each group was the same as above phagocytic function). However, on the 6th day after administration, 0.2 ml 3:5 (VN) sheep red blood cell (RBC) suspension was injected i.p. into each mouse. 4 days later (day 10), blood was drawn from all animals and serum was prepared and then diluted 600 times. 1 ml diluted serum was mixed with 0.5 ml 10% sheep RBC suspension. N.S. was used as blank control. All samples were incubated at 37° C. for 30 minutes, and centrifuged (2000 rev/min) for 5 minutes. The supernatant was collected for measurement of $OD_{540}$ and $HC_{50}$ was calculated. The results were subject to t test and are shown in Table 7.

TABLE 7

Effects of Sample on Serum Hemolysinogenesis in Normal and Immune-compromised Mouse

| | | | P | |
|---|---|---|---|---|
| Group (i.g.) | No. of Mice | $HC_{50}$ (X ± SD) | Compared with Group 1 | Compared with Group 2 |
| N.S. 0.2 ml/10 g | 10 | 33.91 ± 2.23 | | <0.001 |
| CTX 25 mg/kg | 10 | 22.51 ± 4.30 | <0.001 | |
| Sample 0.4 g/kg | 10 | 31.48 ± 4.60 | >0.05 | <0.001 |
| Sample 0.1 g/kg + CTX 25 mg/kg | 10 | 19.50 ± 3.20 | <0.001 | >0.05 |
| Sample 0.4 g/kg + CTX 25 mg/kg | 10 | 23.41 ± 3.75 | <0.001 | >0.05 |

The results in Table 7 show that N-(13-methyl-tetradecanoyl)-4-amino-1,2-benzenediol had no obvious effects on serum hemolysinogenesis in either normal or immune-compromised mouse ($P_{1,3}$, $P_{2,4}$, and $P_{2,5}$>0.05). This suggests that the Sample does not evidently affect host humoral immunity.

3: Delayed Hypersensitivity 50 female ICR strain mice, weighing 18–21 g, were randomly divided into 5 groups of 10 each. The method of administration in each group was the same as above phagocytic function). However, on the 5th day after administration, each mouse was injected with 50 μl 10% sheep RBC suspension through tail vein. 4 days later (day 9), each mouse was injected intradermally with 20 μl 10 sheep RBC suspension or normal saline into metatarus of the left or right hind limbs, respectively. The digital thickness of each mouse was measured 24 hours later, and the difference in thickness between left and right digits was subject to t test analysis. The results are shown in Table 8.

TABLE 8

Effects of Sample on delayed hypersensitivity of normal and immune-compromised mice

| | | Difference in thickness | P | |
|---|---|---|---|---|
| Group (i.g.) | No. of Mice | between left and right palm (mm (X ± SD) | Compared to Group one | Compared to Group two |
| N.S. 0.2 ml/10 g | 10 | 2.04 ± 0.50 | | <0.01 |
| CTX 25 mg/kg | 10 | 1.25 ± 0.48 | <0.01 | |
| Sample 0.4 g/kg | 10 | 1.98 ± 0.61 | >0.05 | <0.01 |
| Sample 0.1 g/kg + CTX 25 mg/kg | 10 | 1.56 ± 0.22 | >0.05 | >0.05 |

TABLE 8-continued

Effects of Sample on delayed hypersensitivity of normal and immune-compromised mice

| Group (i.g.) | No. of Mice | Difference in thickness between left and right palm (mm (X ± SD) | P Compared to Group one | Compared to Group two |
|---|---|---|---|---|
| Sample 0.4 g/kg + CTX 25 mg/kg | 10 | 1.50 ± 0.48 | >0.05 | >0.05 |

Table 8 shows that N-(13-methyl-tetradecanoyl)-4-amino-1,2-benzenediol had no inhibitory effect to the delayed hypersensitivity of both normal and CTX-treated mice. The values of $P_{1,3}$, $P_{2,4}$, and $P_{2,5}$ were all greater than 0.05, suggesting that there were no apparent effects of the sample on host cellular immunity.

4: Weights of Immune Organs

The mice were sacrificed after delayed hypersensitivity test above and the thymus and pancreas were collected and weighed. Indices of each organ (mg/10 g body weight) were calculated and subject to t test, and shown in Table 9 as well.

TABLE 9

Effect of the Sample on the indices of immune organs of both normal and CTX-compromised mice

| Drug (i.g.) | Number of mice | Indices of thymus (mg/ 10 g avoirdupois) | Indices of pancreas (mg/10 g avoirdupois) |
|---|---|---|---|
| N.S. 0.2 ml/10 g | 10 | 3.623 ± 1.369[a] | 4.513 ± 0.895[a] |
| CTX 25 mg/kg | 10 | 1.387 ± 0.701 | 2.287 ± 1.023 |
| Sample 0.4 g/kg | 10 | 3.505 ± 1.212[a] | 4.132 ± 0.487[a] |
| Sample 0.1 g/kg + CTX 25 mg/kg | 10 | 2.591 ± 0.517[a] | 2.395 ± 0.894 |
| Sample 0.4 g/kg + CTX 25 mg/kg | 10 | 3.165 ± 0.635[a] | 3.085 ± 1.152 |

[a]$P < 0.001$, compared to the control group.

The results in Table 9 show that there was no significant effect of the Sample on the indices of immune organs for normal mice (both thymus and pancreases, $P_{1,3}>0.05$). As to the mice that were treated by CTX, these indices increased after combined administration of the Sample. The increase in the indices of thymus among these three groups is statistically significant ($P_{1,2}$ and $P_{2,4}<0.001$). It is suggested that the Sample is different from the anticancer compounds of common clinical use, in that the Sample does not inhibit host immune function at therapeutic dosage.

Similarly, it was shown that the specific structured compounds disclosed in the present invention have no influence on immune function of normal body and would not aggravate the immune suppression induced by chemotherapy drugs. Furthermore they have immune boosting effects and alleviate the immune suppression when used in combination with other chemotherapy drugs.

Experiment 8

Acute Toxicity Tests of 15-methyl-2-hexadecenoic acid on Mice

The acute toxicity tests were assessed for two administration routes, through gavage and subcutaneous injection.

1: Gavage Administration

A preliminary test failed to establish $LD_{50}$ of 15-methyl-2-hexadecenoic acid (Sample). Thus, the acute toxicity test was conducted in twenty ICR strain mice, weighing 18–20 g. The Sample was given through gavage at dosage of 2.5 g/kg, twice a day. Continuous monitoring was made for 14 days. No major anomaly was observed, indicating safety of the Sample with $LD_{50}>5$ g/kg.

2: Subcutaneous Injection

Twenty ICR strain mice, weighing 18–20 g were used in the test. The daily dosage of the Sample at 1 g/kg was subcutaneous injected at both sides of spine for 14 days. No mice death was observed, indicating safety of the Sample and $LD_{50}>2$ g/kg (s.c.).

Experiment 9

Mechanism of Anti-Cancer Activity of 15-methyl-2-hexadecenoic acid

1: 15-methyl-2-hexadecenoic acid (the Sample) Causes Apoptosis

The test Sample kills cancer cells by induction of apoptosis in these cells. This is demonstrated in the following two experiments:

(1) in situ Cell Death Detection

Leukemia K562 cells and gastric carcinoma SNU423 cells were treated with the Sample and slides were prepared with cell suspension. The slides were examined with in situ cell death detection kit (Boehringer Mannheim). Large portion of cancer cells after treatment of 4 hours and 8 hours were stained, suggesting that the Sample induced apoptosis in these cells.

(2) DNA Fragmentation Assay

After treatment of the Sample in the above two cell lines, cellular DNA was purified and tested with ApoAlert LM-PCR kit (Clontech). Samples collected at 8 hours and 24 hours past treatment showed fragmented DNA in gel electrophoresis, which confirmed the apoptosis induced by the Sample.

2: Apoptotic Induction by 15-methyl-2-hexadecenoic acid is Closely Related to the Caspase Pathway The mechanism by which the Sample induces apoptosis is closely related to the caspase pathway. This is suggested by the following:

(1) translocation of cytochrome c from mitochondria to cytosol

After treatment with the Sample, as early as 4 hours, cytochrome c can be detected in the cytosol by western analysis. This suggested that cytochrome c translocated from mitochondria to cytosol, which has been repeatedly implicated as an upstream event of caspase activation.

(2) cleavage of many substrates of caspase, including Lamin-B, Rb, and PARP By western analysis, cleavage products of Lamin-B, Rb, and PARP can be detected as early as 4 hours after treatment by the Sample. Presence of these cleavage products pointed to caspase activity, as many other reports had suggested. Dephosphorylation of Rb was also observed, in accordance with the report of induction of apoptosis in segregated cancer cells by dephosphorylated Rb.

The compounds with the specific structure in the present invention, whether chemically synthesized or extracted from natural resources, or administered in a natural mixture without extraction, have significant anti-cancer activity for human or animal. These compounds can also be taken orally or by injection, in the forms of liquid, powder, tablet, injection, capsule, or encapsulated liposome, or they can be topically applied in the forms of cream, ointment, or lotion.

EXAMPLES

Example 1

Synthesis of 13,13-dimethyl-tetradecanoic Acid

Electrolysis reaction was carried out with methyl dodecandioic monoester (139 g, 0.56 mole), 1,2-dimethyl propanoic acid (56 g, 0.56 mole), sodium (0.65 g, 0.028 mole), and anhydrous methanol (1390 ml) at a direct current of 2.0 A until the reaction mixture was basic. Methanol was removed by evaporation; the mixture was washed with water and subject to vacuum fractional distillation. 120° C./0.4 mmHg fraction was collected as 13,13-dimethyl-tetradecanoate (21.5 g). 13,13-dimethyl-tetradecanoate was then refluxed with 10% NaOH (53.5 ml) and methanol (64.5 ml) for 2 hours, and methanol is again removed by evaporation. The remainder was adjusted to pH 2.0 with 10% HCl, cooled down, and precipitates were collected by filtration. Filtrate was washed with water to neutral (became white solid) and subject to vacuum fractional distillation. 170° C./0.4 mmHg fraction was collected and recrystallized with ethanol-water mixture to yield final product, 13,13-dimethyl-tetradecanoic acid (15.8 g, m.p. 37–39° C.).

Example 2

Synthesis of N-(3, 4-dihydroxyl-phenyl)-13-methyl-tetradecanamide p-nitrophenol (69.55 g, 0.5 mole) was dissolved in 10 N HCl (200 ml) in a 1000 ml flask with heating and then cooled down. To the mixture was added 600 ml potassium chlorate (61.25 g, 0.5 mole) solution, gradually with stirring. Stirring was continued for 1 hour after completion of addition and mixture was left overnight at room temperature. After filtration with vacuuming, the filtrate was washed with distilled water and recrystallized with dilute acetic acid solution to yield pale yellow acicular crystal, 2-chloro4-nitro-phenol (80.2 g, m.p. 110–111° C., yield rate 91%).

2-chloro-4-nitro-phenol (64.44 g, 0.4 mole) and 300 ml 4M NaOH solution were refluxed with heating for 6 hours. After cooling down and filtration with vacuuming, the filtrate (crystal) was dissolved in a little warm water (60° C.). The solution was adjusted to pH 2.0 with 10% HCl and cooled down while stirring. After filtration, the filtrate was recrystallized with water to yield 4-nitro-1,2-benzenediol (52.1 g, yield rate 84%).

To a 1000 ml flask was added 4-nitro-1,2-benzenediol (49.6 g, 0.32 mole), and then 403 ml water and 16 ml 10 N HCl (0.16 mole). While stirring 83.2 g zinc dust (1.28 mole) was added gradually and reaction mixture refluxed with heating for 8 hours. After cooling down and filtration with vacuuming, the filtrate was washed thoroughly with 95% ethanol and decolorized by active carbon. Filtration again and evaporation of ethanol was carried out until the solution just started to become turbid. After cooling in freezer and filtration with vacuuming, filtrate was collected as 4-amino-1,2-benzenediol (30.0 g, yield rate 75%).

Dissolve 4-amino-1,2-benzenediol (23.2 g, 0.18 mole) in 95% ethanol. Under salt ice bath 140 ml 2M NaOH solution and 150 ml dichloromethane solution of 13-methyltetradecanoyl chloride (23.2 g, 0.18 mole) were added simultaneously to the benzenediol solution. Stir at room temperature for 6 hours. Adjust pH to 3.0 with HCl, freeze, and filtrate. Wash the filtrate to neutral with water and recrystallize with 50% ethanol to yield N-(3,4dihydroxyl-phenyl)-13-methyl-tetradecanamide (55.8 g, m.p. 85–86° C., yield rate 85%).

Example 3

1. Synthesis of N-(13-methyl)-tetradecanoyl Glycine 13-methyltetradecanoic acid (600 mg, 2.48 mmole) and dichlorosulfoxide (2.0 ml) were added to a 10 ml round bottom flask and heated with reflux for 4 hours. To this solution was added 10 ml petroleum ether to remove dichlorosulfoxide. The product (13-methyl-tetradecanoyl chloride) was used in following reaction.

Glycine (186.1 mg, 2.48 mmole) and 2M NaOH (2.48 ml, 4.96 mmole) were added to a 50 ml flask and stirred to complete dissolution. To this solution, 2M NaOH (2.48 ml, 4.96 mmole) and above acyl chloride product in 10.0 ml of dichloromethane were added simultaneously by two funnels under ice bath. After complete addition the ice bath was removed and the reaction mixture was stirred for 6 hours at room temperature. Large amount of white precipitates should form in the reaction mixture at this step. Ethanol was added to dissolve the precipitates and the organic solvent was removed by evaporation. Small amount of water was added and the reaction mixture became clear. After adding 10% dilute HCl by drops, white precipitates formed again and were collected by filtration. The filtrate was purified by recrystallization with ethanol-water mixture to yield final white solid product, N-(13-methyl)-tetradecanoyl glycine (0.52 g, m.p. 78–81° C., yield rate 70.1%). $^1$H-NMR (CDCl$_3$):δ5.98(m, 1H, NH), 4.09(m, 2H, CH$_2$), 2.27 (m, 2H, COCH$_2$), 1.62(m, 2H, CH$_2$), 1.50(m, 1H, CH), 1.15–1.32 (m, 18H), 0.86(d, 6H, 2CH$_3$); MS(m/e): 299(M$^+$, 2), 130 (25), 117(100), 99(60), 76(30), 44(30).

2. Synthesis of N,N-diethyl-13-methyl-tetradecanamide 13-methyltetradecanoic acid (726 mg, 3.0 mmole) and dichlorosulfoxide (2.0 ml) were added to a 10 ml round bottom flask and heated with reflux for 4 hours. To this solution was added 100 ml petroleum ether to remove dichlorosulfoxide. The product (13 methyl-tetradecanoyl chloride) was used in following reaction.

Diethylamine (548 mg, 7.5 mmole), N,N-dimethylaminopyridine (DMAP) (30 mg) and dichloromethane (5 ml) were added to a 50 ml flask and stirred to complete dissolution. To this solution, above acyl chloride product in 10.0 ml of dichloromethane were added under ice bath. After complete addition the ice bath was removed and the reaction mixture was stirred for 8 hours at room temperature. 10 ml 10% dilute HCl was then added and reaction stirred for 30 minutes. 20 ml water was added, followed by extraction with ethyl acetate (EtOAc) (30 ml×3). The combined organic layer was washed with water to neutral and dried with anhydrous magnesium sulfate. After concentration, pale yellow oily liquid, N,N-diethyl-13-methyl-tetradecanamide (0.73 g, yield rate 81.9%) was obtained. $^1$H-NMR (CDCl$_3$): δ3.34(m, 4H, 2NCH$_2$), 2.85(t, 2H, COCH$_2$), 1.62 (m, 2H, CH$_2$),1.49(m, 1H, CH), 1.07–1.26(m, 24H), 0.86(d, 6H, 2CH$_3$); MS(m/e): 297(M$^+$, 2), 128(25), 115(100), 100 (25), 58(35), 43(20).

3. Synthesis of N-(13-methyl)-tetradecanoyl Piperidine 13-methyltetradecanoic acid (1.0 g, 4.1 mmole) and dichlorosulfoxide (2.0 ml) were added to a 10 ml round bottom flask and heated with reflux for 4 hours. To this solution was added 10 ml petroleum ether to remove dichlorosulfoxide. The product (13-methyltetradecanoyl chloride) was used in the following reaction.

Piperidine (850.6 mg, 10 mmole), N,N-dimethylaminopyridine (DMAP) (30 mg) and dichloromethane (5 ml) were added to a 50 ml flask and stirred to complete dissolution. To this solution, above acyl chloride product in 10.0 ml of dichloromethane were added under ice bath. After complete addition the ice bath was removed and the reaction mixture was stirred for 8 hours at room temperature. 10 ml 10% dilute HCl was then added and reaction stirred for 30 minutes. 20 ml water was added, followed by extraction with ethyl acetate (EtOAc) (30 ml×3). The combined organic layer was washed with water to neutral and dried with anhydrous magnesium sulfate. After concentration, pale yellow oily liquid, N-(13-methyl)-tetradecanoyl piperidine (1.01 g, yield rate 79.7%) was obtained. The final product will solidify when placed in refrigerator. m.p.<0° C. $^1$HNMR(CDCl$_3$): δ3.52(brs, 2H, NCH$_2$), 3.38(brs, 2H, NCH$_2$), 2.29(t, 2H, COCH$_2$), 1.44–1.62(m, 9H), 1.12–1.28 (m, 18H), 0.83(d, 6H, 2CH$_3$); MS(m/e): 309(M$^+$, 2), 294 (10), 140(70), 127(100), 112(25), 84(40), 43(35).

Example 4

Synthesis of (3,4-dihydroxyphenyl)-13-methyl-tetradecanamine

Dichlorosulfoxide (143.5 ml, 2.0 mole) was added to 13-methyl-1-tetradecanol (114.0 g, 0.5 mole) and heated with reflux for 4 hours. To this solution was added 200 ml petroleum ether to remove dichlorosulfoxide. After vacuum fractional distillation, 159–161° C./1.0 mmHg fraction was collected as 13-methyl-1-chloro-tetradecane (102 g, yield rate 82.8%).

4-amino-1,2-benzenediol (25 g, 0.2 mole) was dissolved in 200 ml methanol. To this solution, 13-methyl-1-chloro-tetradecane (54.2 g, 0.22 mole) was added drop-by-drop with stirring. The mixture was further stirred for 3 hours and methanol was removed by evaporation. After filtration with vacuuming, the filtrate was washed with distilled water and recrystallized with 95% ethanol to yield (3,4-dihydroxyphenyl)-13-methyl-tetradecanamine (49.6 g, yield rate 74%).

Example 5

1. Synthesis of 15-methyl-2-hexadecenoic Acid 300 ml dry toluene and sodium (138 g, 6.0 mole) were added to a flask. While stirring, 200 ml anhydrous methanol solution of 13-methyl-tetradecanoate (256 g, 1.0 mole) was added to the flask gradually in 5 minutes. 800 ml more methanol was added and the mixture refluxed with heating until sodium completely disappeared. 200 ml water was added and mixture was again refluxed with heating for 30 minutes. Methanol and toluene were removed by evaporation and water phase was also removed by extraction. Lipid phase was subject to vacuum fractional distillation and 140–142° C./1.0 mmHg fraction was collected as 13-methyl-1-tetradecanol (142.6 g, yield rate 63%).

Chloro-chromic pyridine (161.6 g, 0.75 mole) and 450 ml dichloromethane were added to a flask. With stirring, 150 ml dichloromethane solution of 13-methyl-1-tetradecanol (114 g, 0.50 mole) was slowly added to the flask and stirring continued for 1.5 hours at room temperature. Let the mixture stand and separate into two phases. Decant upper phase and wash the remainder with 100 ml diethyl ether. Combine all liquid and wash sequentially with saturated NaCl, 10% HCl, and saturated NaCl solution with 5% NaHCO$_3$. Desiccate with anhydrous CaCl$_2$ and remove solvent by evaporation to yield 13-methyl-tetradecanaldehyde (57.6 g, yield rate 51%).

13-methyl-tetradecanaldehyde (56.5 g, 0.25 mole), malonic acid (26.5 g, 0.51 mole), and pyridine (30.8 ml, 0.374 mole) were added to a flask and refluxed with heating for 3 hours. After cooling down 30% sulfuic acid was added and the reaction mixture was stirred for 3 hours under ice bath and then extracted by diethyl ether. Diethyl ether was removed by evaporation and product was subject to vacuum fractional distillation and 170–172° C./1.0 mmHg fraction was collected as 15-methyl-2-hexadecenoic acid (50.9 g, yield rate 76%).

2. Synthesis of 9-methyl-2-decenoic Acid

Methyl mono-adipate (102 g, 0.42 mole), isovaleric acid (84.4 g, 0.84 mole), sodium (0.5 g, 0.022 mole), and 1020 ml methanol were subject to electrosynthesis at a direct current of 1.5 A until the reaction mixture was basic. Methanol evaporated, the mixture was washed with water and subject to vacuum fractional distillation. 108° C./23 mmHg fraction was collected as 7-methyl-octanoate (53 g, yield rate 52%).

In a similar reaction as in 1 above, 100 ml toluene, sodium (39.5 g, 1.72 mole), 7-methyl-octanoate (52 g, 0.29 mole), and 260 ml anhydrous methanol reacted to yield 7-methyl-1-octanol (44.3 g, yield rate 85%); 7-methyl-1-octanol (44.3 g, 0.31 mole) reacted with chloro-chromic pyridine (100 g, 0.465 mole) to yield 7-methyl-octanaldehyde (31 g, yield rate 70%); and finally, 7-methyl-octanaldehyde (20 g, 0.14 mole), malonic acid (15 g, 0.14 mole), and 15 ml pyridine were added together and refluxed with heating for 3 hours. After cooling down 15 ml 30% sulfuric acid was added and the reaction mixture was stirred for 3 hours under ice bath and then extracted by diethyl ether. Diethyl ether was removed by evaporation and product was subject to vacuum fractional distillation and 122° C./1.5 mmHg fraction was collected as 9-methyl-2-decenoic acid (16 g, yield rate 80%).

Example 6

Synthesis of N,N-di-(β-hydroxyethyl)-12-methyl-tridecyl Amine

Dichlorosulfoxide (800 ml) was added to 13-methyl-tetradecanoic acid (400 g, 1.653 mole) and heated with reflux for 4 hours. To this solution was added 1000 ml petroleum ether to remove dichlorosulfoxide. After vacuum fractional distillation, 130–132° C./1.0 mmHg fraction was collected as 13-methyl-tetradecanoyl chloride (375 g, 1.356 mole, yield rate 82.1%).

Ammonium water (450 ml, 28%) was added to a flask and kept under ice bath. With stirring, 13-methyl-tetradecanoyl chloride (300 g, 1.85 mole) dissolved in 500 ml dichloromethane was added drop-by-drop and reacted for 1 hour at room temperature. After drying the reaction mixture, extraction by acetyl acetate and recrystallization, 13-methyl-tetradecanoyl amide (208 g, yield rate 79.5%) was collected.

Sodium (43.9 g, 1.91 mole) was added to anhydrous methanol (2000 ml) in a flask. After disappearance of sodium, 13-methyl-tetradecanoyl amide (200 g, 0.830 mole) was added and the reaction mixture cooled down to −2° C. under ice salt bath. With stirring, dry bromine (146.1 g, 0.913 mole) was added drop-by-drop and stirring continued for 2.5 hours. Ice bath was removed and reaction mixture heated to 70° C. 10% NaOH (830 ml, 2.04 mole) was added and refluxed for 4 hours. Methanol was then removed by evaporation and remainder extracted by benzene. After removal of benzene by evaporation, vacuum fractional distillation was performed and 160–162° C./15 mmHg fraction was collected as 12-methyl-tridecyl amine (106 g, yield rate 60.1%).

12-methyl-tridecyl amine (106 g, 0.5 mole) was melted at 50° C. With stirring, chloroethanol (76.5 g, 1 mole) was added gradually and stirring continued for half an hour. Reaction was continued for 8 hours at 95–100° C. to completion. The reaction mixture was neutralized to pH 7 with 10% NaOH and lipid layer was separated. Water layer was extracted with benzene for three times and combined with the separated lipid layer. After removal of benzene and vacuum fractional distillation, N,N-di-(β-hydroxyethyl)-12-methyl-tridecyl amine was collected.

Example 7

Synthesis of 13-methyl-tetradecyl-(2,4-dihydroxyl)benzene 13-methyl-tetradecanoic acid (36.2 g, 0.15 mole) and anhydrous zinc chloride (32.7 g, 0.24 mole) were added to a 500 ml flask and heated to 110° C. with oil bath and kept for half an hour. While stirring, 1,3-benzenediol (22 g, 0.2 mole) was added and reaction heated to 160° C. and continued for 2 hours with stirring. After completion, reaction was cooled down gradually to 110° C. and diluted with 300 ml 15% HCl (1.04 mole) with stirring and cooled to room temperature and further to below 5° C. After filtration, the filtrate was washed three times with 5% HCl, and water was removed. With vacuum fractional distillation, 230° C./1.0 mmHg fraction was collected and decolorized and recrystallized with 80% ethanol to yield 1-(2,4-dihydroxyphenyl)-1-(12-methyl)-tridecanone (11 g, m.p. 87° C., yield rate 87.8%).

1-(2,4-dihydroxyphenyl)-1-(13-methyl)-tetradecanone (20 g, 0.06 mole), Zn—Hg (200 g, 3.08 mole) and hydrochloric acid (200 ml, 1.67 mole) were added to a 500 ml flask and refluxed with vigorous stirring for 8 hours and cooled down. Following extraction by toluene, removal of toluene and vacuum fractional distillation, 246° C./0.5 mmHg fraction was collected and recrystallized with 95% ethanol to yield 13-methyl-tetradecyl-(2,4dihydroxyl)benzene (12 g, m.p. 70° C., yield rate 62.9%).

Example 8

Synthesis of 13-methyl-tetradecyl-3,4,5-trihydroxybenzoate

To an anhydrous toluene solution (300 ml) of freshly cut sodium (138 g, 6 mole), an anhydrous methanol solution (800 ml) of 13-methyl-tetradecanoate (256 g, 1 mole) was added gradually with stirring and cooling. After completion of the addition, heat with reflux until sodium disappears. Add 400 ml water and reflux for 30 minutes. Toluene and methanol were removed by evaporation and the lipid layer was subject to vacuum fractional distillation. 142–144° C./1 mmHg fraction was collected as 13-methyl-1-tetradecanol (yield rate 65.0%). 13-methyl-1-tetradecanol (107 g, 0.50 mole) and 3,4,5-trihydroxybenzoic acid (gallic acid, 94 g, 0.50 mole) were added to 200 ml toluene and 5.8 ml concentrated sulfuric acid and refluxed with heating. Water was removed from the reaction mixture until the temperature of reflux reached 110° C. and toluene was completely removed. The remainder was extracted by ethyl ether and washed with water. After drying and removal of ethyl ether and recrystallization with 95% ethanol, 13-methyl-tetradecyl-3,4,5-trihydroxybenzoate (135.4 g, m.p. 64–66° C., yield rate 74.0%) was collected.

The disclosure of Provisional Patent Application No. 60/180,677, filed Feb. 7, 2000, whose date this application seeks benefit of, is hereby incorporated by reference.

Obviously, numerous modifications and variations of the present invention are possible in light of the above teachings. It is therefore to be understood that within the scope of the appended claims, the invention may be practiced otherwise than as specifically described herein.

The invention claimed is:

1. A compound having a formula selected from the group consisting of the following formulae (1), (2) and (3):

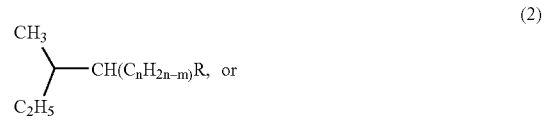

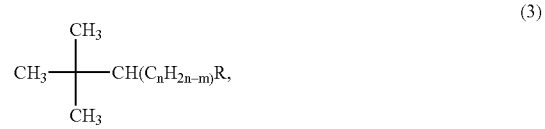

wherein n is an integer from 5 to 19, m is an even-numbered integer from 0 to 2b, inclusive, wherein b is the maximum number of unsaturated bonds, and wherein a double bond is counted as 1 and a triple bond is counted as 2, and R is a polar group, and when m=2 and R is COOH, the compound of formula (1) is selected from the group consisting of 9-methyl-6-decenoic acid, 9-methyl-2-decenoic acid, and 15-methyl-2-hexadecenoic acid, and excluding compounds of formulae (1) and (2) wherein m=0, and R is COOH or an aliphatic ester thereof or salt thereof, or R is OH or an aliphatic ether thereof or aliphatic ester thereof, and excluding 13, 13-Dimethyl-tetradecanoic acid.

2. The compound of claim 1, selected from the group consisting of unsaturated branched-chain fatty acids containing a double bond between the α and β carbons from the carboxyl end, and their pharmaceutically acceptable esters and metal salts.

3. The compound of claim 2, which is 15-methyl-2-hexadecenoic acid.

4. The compound of claim 1, wherein R is selected from the group consisting of (1) an amide group R=—CONR$_1$R$_2$ wherein NR$_1$ is one of the following: hydroxyl-substituted phenylamine group, wherein the number of hydroxyl group(s) is 1 to 5, at any possible position(s)); amino acid; amino-glucose; 3-hydroxyl-4-carboxyl-phenylamine group; sulfonic phenylamine group; or amino heterocyclic group, while R$_2$ is hydrogen, or R$_1$ and R$_2$ are independently methyl or ethyl group, or R$_1$ and R$_2$ together with N is piperidine; pyrrolidine or morpholine, (2) an ester group R=—COOR$_3$ wherein R$_3$ is a phenyl group with substitution(s) of sulfonic, carboxyl, or 1–5 hydroxyl group(s), at any possible position(s), (3) a ketone group R=—COR$_4$
wherein R$_4$ is a phenyl group with substitution(s) of 1–5 hydroxyl group(s), at any possible position(s),
(4) a hydroxyl-substituted benzoyloxy group, wherein the number of hydroxyl group(s) is 1 to 5, at any possible position(s),
(5) a hydroxyl-substituted phenyl group, wherein the number of hydroxyl group(s) is 1 to 5, at any possible position(s),
(6) an amine group R=—NHR$_5$ or its physiologically acceptable salt, wherein R$_5$ is methyl, ethyl, hydroxyethyl, or phenyl, with substitution(s) of sulfonic, carboxyl, or 1–5 hydroxyl group(s), at any possible position(s); or an amine group,

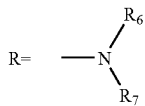

or its physiologically acceptable salt, wherein R$_6$ and R$_7$ are independently methyl, ethyl, or hydroxyethyl group,
(7) an amino-acyl group R=—NH—CO—R$_8$
wherein R$_8$ is a phenyl group with substitution(s) of sulfonic, carboxyl, or 1–5 hydroxyl group(s), at any possible position(s),
(8) an α-substituted carboxylic group,

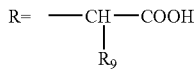

wherein R$_9$ is halogen, amino, or hydroxyl group.

5. The compound of claim 1, selected from the group consisting of:
N-(3,4-Dihydroxyphenyl)-13-methyl tetradecanamide,
N-(4-Sulfo-phenyl)-13-methyl tetradecamide,
N-(13-methyl-tetradecanoyl) glycine,
N-(13-methyl-tetradecanoyl)-L-alanine,
N-(13-methyl-tetradecanoyl)-L-phenylalanine,
N-(13-methyl-tetradecanoyl)-L-valine,
N-(13-methyl-tetradecanoyl)-L-leucine,
N-(13-methyl-tetradecanoyl)-L-isoleucine,
N-(13-methyl-tetradecanoyl)-L-glutamic acid,
N-(13-methyl-tetradecanoyl)-L-proline,
N-(13-methyl-tetradecanoyl)-2-amino-2-deoxyglucose,
N-(3-Hydroxy-4-carboxylphenyl)-13-methyl-tetradecanamide,
N,N-Diethyl-13-methyl-tetradecanamide,
N-(13-Methyl tetradecanoyl) piperidine,
N-(13-Methyl-tetradecanoyl) pyrrolidine,
N-(13-Methyl-tetradecanoyl) morpholine,
N-(13-Methyl-tetradecanoyl)-2-amino-pyrimidine,
(2,4-dihydroxy phenyl)-12-methyl tridecanone,
(2,4,6-trihydroxy phenyl)-12-methyl tridecanone,
(2,3,4-trihydroxy phenyl)-12-methyl tridecanone,
(13-Methyl tetradecyl)-2,4-dihydroxy phene,
(13,13-Dimethyl tetradecyl)-2,4-dihydroxy phene,
(12-Methyl tetradecyl)-2,4-dihydroxy phene,
(13-Methyl tetradecyl)-2,3,4-trihydroxy phene,
N-(12-Methyl tridecyl)-4-amino benzenesulfonic acid,
N-(12-Methyl-tridecyl)-4-amino-1,2-benzenediol,
2-Bromo-13-methyl-tetradecanoic acid,
2-Amino-13-methyl-tetradecanoic acid,
2-(12-Methyl-tridecyl)-5-mercapto-1,3,4-thiadiazole,
2-(12-Methyl-tridecyl)-5-hydroxy-1,3,4-oxadiazole and
N-(13-Methyl tetradecyl)-4-amino-1,2-benzenediol.

* * * * *